(12) United States Patent
Zevenbergen

(10) Patent No.: US 9,964,509 B2
(45) Date of Patent: May 8, 2018

(54) DRIFT COMPENSATED ION SENSOR

(71) Applicant: Stichting IMEC Nederland, Eindhoven (NL)

(72) Inventor: Marcel Zevenbergen, Nuenen (NL)

(73) Assignee: Stichting IMEC Nederland, Eindhoven (NL)

( * ) Notice: Subject to any disclaimer, the term of this patent is extended or adjusted under 35 U.S.C. 154(b) by 147 days.

(21) Appl. No.: 14/975,815

(22) Filed: Dec. 20, 2015

(65) Prior Publication Data

US 2016/0178572 A1   Jun. 23, 2016

(30) Foreign Application Priority Data

Dec. 19, 2014 (EP) .................................. 14199277

(51) Int. Cl.
*G01N 27/333* (2006.01)
*G01N 27/30* (2006.01)
*G01N 27/413* (2006.01)

(52) U.S. Cl.
CPC ......... *G01N 27/301* (2013.01); *G01N 27/333* (2013.01); *G01N 27/413* (2013.01)

(58) Field of Classification Search
CPC ... G01N 27/301; G01N 27/302; G01N 27/333
See application file for complete search history.

(56) References Cited

U.S. PATENT DOCUMENTS

| | | | |
|---|---|---|---|
| 4,218,299 A * | 8/1980 | Lindell | G01N 27/36 204/420 |
| 4,822,456 A | 4/1989 | Bryan | |
| 5,100,530 A | 3/1992 | Dorr et al. | |
| 2002/0011422 A1 | 1/2002 | Meier | |
| 2009/0101524 A1 | 4/2009 | Woodward et al. | |

FOREIGN PATENT DOCUMENTS

| | | |
|---|---|---|
| DE | 8409810 U1 | 12/1985 |
| DE | 10 2004 015 084 A1 | 8/2005 |

(Continued)

OTHER PUBLICATIONS

European Search Report, European Patent Application No. 14199277.6, dated Jun. 10, 2015, 5 pages.

(Continued)

*Primary Examiner* — J. Christopher Ball
(74) *Attorney, Agent, or Firm* — McDonnell Boehnen Hulbert & Berghoff LLP

(57) ABSTRACT

An ion sensor for sensing an ion concentration in a bulk solution comprises a reference electrode embedded in an reference electrolyte solution, and a first ion-selective electrode. The ion sensor moreover comprises a second electrode sensitive to the reference ions or to an ion different from the ion to be measured, whereby the second electrode is in direct contact with the bulk solution when the ion sensor is immersed therein. The potential difference between the first electrode and the reference electrode is a measure for the ion concentration in the bulk solution and is corrected with the potential difference between the second electrode and the reference electrode to compensate for the drift of the reference electrode.

15 Claims, 10 Drawing Sheets

(56) References Cited

FOREIGN PATENT DOCUMENTS

GB          2460130 B      10/2010
WO          94/17400 A1    8/1994

OTHER PUBLICATIONS

Simonis, Anette et al., "Miniaturised Reference Electrodes for Field-Effect Sensors Compatible to Silicon Chip Technology", Electrochimica Acta, vol. 51, 2005, pp. 930-937.
Martz, Todd R. et al., "Testing the Honeywell Durafet for Seawater pH Applications", Limnology and Oceanography: Methods, vol. 8, 2010, pp. 172-184.

* cited by examiner

DRIFT COMPENSATED ION SENSOR

CROSS-REFERENCE TO RELATED APPLICATION

The present application is a non-provisional patent application claiming priority to European Patent Application No. 14199277.6 filed Dec. 19, 2014, the contents of which are hereby incorporated by reference.

TECHNICAL FIELD

The present disclosure relates to the field of electrochemical sensors. More specifically it relates to systems and methods for compensating the drift of a reference electrode in a miniaturized ion sensor.

BACKGROUND

Potentiometric sensors are used for detecting chemical or biochemical compounds in a solution. Such potentiometric sensors are electrochemical sensors that generate voltages that scale with the concentration of an ion to be determined. A pH sensor is an example of such a potentiometric sensor. A potentiometric sensor usually comprises an ion-selective electrode and a reference electrode. The reference electrode has a potential which can be used as a reference potential for the ion-selective electrode. The potential difference between the ion-selective electrode and the reference electrode is a measure for the concentration of the compound for which the ion-selective electrode is sensitive. An important requirement is that the potential of the reference electrode is stable and constant.

In operation, the reference electrode is immersed, together with the ion-selective electrode, in the solution under test. For proper operation, the interfacial potential of the reference electrode should be independent of the solution composition.

A commonly used type of reference electrode is a silver chloride electrode (Ag/AgCl). This electrode has a fixed potential when in contact with a reservoir with a fixed chloride concentration, such as 3 Molar KCl (3M KCl). An example thereof is shown in FIG. 1. FIG. 1 shows a prior art reference electrode comprising an Ag/AgCl wire 110 immersed in a reservoir 120 containing a predetermined chloride concentration, for instance 3 Molar KCl (the reference electrolyte solution). An electrolyte bridge or a porous ceramic plug separates the reference electrolyte solution from the solution which needs to be measured. In the example reference electrode of FIG. 1, the electrolyte bridge is a porous frit (salt bridge) 130 separating the inner reservoir and the bulk solution. Ions can still pass through this junction; therefore an ionic contact forms. The potential of the Ag/AgCl electrode depends on the chloride concentration in the reference electrolyte solution. The electrolyte bridge or the porous ceramic plug prevents chloride ions from instantaneously migrating between the liquid of the reference electrode and the solution. If the reference electrode is immersed in a solution with a different chloride concentration, chloride ions will leach out which leads to a change in chloride concentration in the reservoir and therefore drift of the reference electrode. Depending on the volume of the reference electrolyte solution, these migrations will cause the chloride concentration in the reference electrolyte solution to change, thereby changing the reference voltage. As the reservoir is rather large in the example of FIG. 1, drift is limited. One way of stabilizing the reference voltage is to increase the volume of the reference electrolyte solution. This is, however, not possible in microfabricated reference electrodes since the size is limited in these electrodes.

Microfabricated reference electrodes typically comprise a planar electrode, made by photolithography or screen-printing techniques covered by a hydrogel, such as agarose or polyhydroxyethylmethacrylate (pHEMA). An example disclosed by Simonis et. al. "Miniaturised reference electrodes for field-effect sensors compatible to silicon chip technology," Electrochimica Acta 51, vol. 51, issue 5, 10 Nov. 2005, pp. 930-937, is shown in FIG. 2. FIG. 2 shows a printed circuit board 216 comprising a stack of a silicon layer 222, covered with a $SiO_2$ layer 220, covered with an Ag/AgCl layer 218. The Ag/AgCl layer is covered by a hydrogel 214 which comprises KCl and may be, for instance, agarose (agar)+KCl or polyhydroxymethylmethacrylate (pHEMA)+KCl. The hydrogel layer 214 is sealed with a PVC layer 210 and the PVC layer is covered with a nafion or cellulose nitrate layer 212.

The covered hydrogel layer 214, 210 is sealed at its sidewalls by means of a sealing (e.g., an O-ring) 208. The sealing 208 is sealed against the Ag/AgCl layer. Outside the sealing 208 an epoxy resin 204 is applied, thus screening the outside part of the Ag/AgCl electrode (the part not covered by the sealing 208 and the hydrogel 214) from the environment. Silicone 206 is applied partly covering the epoxy resin 204, the sealing 208, and the nafion or cellulose nitrate 212. An electrical contact 202 is in contact with the Ag/AgCl electrode 218 and allows for measuring the potential of the electrode 218.

Increasing the stability of miniaturized reference electrodes is preferably done without increasing the volume of the reference electrolyte solution. Many studies on miniaturized reference electrodes have focused on the composition of the reference electrolyte solution (e.g., a hydrogel), and covering it with membranes to slow down the out-diffusion of chloride ions. Besides these efforts there is still room for improving the stability of miniaturized reference electrodes.

SUMMARY OF THE DISCLOSURE

The present disclosure provides a sensitive, accurate, and stable ion sensor.

In a first aspect, the present disclosure provides an ion sensor for sensing an ion concentration in a bulk solution. The ion sensor may comprise a reference electrode embedded in a reference electrolyte solution having reference ions, and the electrolyte solution may induce a voltage on the reference electrode which is dependent on the concentration of reference ions in the reference electrolyte solution. The ion sensor may further comprise a first electrode which is ion-selective for the ion to be measured and a second electrode which is ion-selective to the reference ions or to an ion different from the ion to be measured. The first electrode and the second electrode may be configured to be in direct contact with the bulk solution when the ion sensor is immersed in the bulk solution. The ion sensor may further comprise a controller for determining a first potential difference between the first electrode and the reference electrode as a measure for the ion concentration in the bulk solution, and for correcting the first potential difference between the first electrode and the reference electrode with a second potential difference between the second electrode and the reference electrode to compensate for the drift of the reference electrode.

It is an advantage of embodiments of the present disclosure that a sensitive, accurate, and stable ion sensor is provided. The stability refers to the stability of the reference electrode. The reference voltage of the reference electrode drifts when the concentration of the reference ion in the reference electrolyte solution drifts. It is an advantage of embodiments of the present disclosure that a reference voltage can be obtained that is stabilized with regard to concentration changes of the reference ion in the reference electrolyte solution. It is an advantage of embodiments of the present disclosure that drift of the reference voltage of the reference electrode can be stabilized without a need for increased volume of the reference electrolyte solution. It is an advantage of embodiments of the present disclosure that the volume of the reference electrolyte solution can be in the order of microliters. It is an advantage of embodiments of the present disclosure that drift of the reference electrode can be directly measured and compensated for by means of a measurement on a second electrode in contact with the bulk solution. This allows for reducing the volume of the electrolyte solution even more.

In embodiments of the present disclosure, the second electrode may be ion-selective to the reference ions. In this case, the voltage difference between the second electrode and the reference electrode is a measure of the concentration difference of the reference ions in the electrolyte solution and the reference ions in the bulk solution. This concentration difference is a driving force for the drift. Therefore it is an advantage of embodiments of the present disclosure that the voltage difference between the second electrode and the reference electrode is, when immersing the ion sensor in a bulk solution, a measure of the drift the reference electrode is going to experience. When the voltage difference approaches 0V the reference sensor has equilibrated with the bulk solution and no drift is expected anymore.

Miniaturized ion sensors can be made that can be used in applications for which conventional reference electrodes are not suited, because they are too large and rigid. Ion sensors can, for example, be miniaturized such that they can be used in sweat patches, or they can be positioned near a wound for smart wound monitoring, or they can be integrated in diapers.

It is an advantage of embodiments of the present disclosure that the drift of the reference electrode can be compensated for by measuring the potential difference between the second electrode and the reference electrode, the reference electrode being the same as the one used for measuring the potential difference with respect to the first electrode. The second electrode may be ion-selective to the reference ion. Both the second electrode and the reference electrode may, for example, be made of the same material, the present disclosure, however, not being limited thereto. When the ion sensor is immersed in the bulk solution, the concentration of the reference ion in the reference electrolyte solution might change because of diffusion of the reference ion into the bulk solution. This concentration change causes the voltage of the reference electrode to drift. This drift can be compensated for with the second electrode which is in direct contact with the bulk solution.

In embodiments of the present disclosure, the reference electrolyte solution may comprise a hydrogel. This is advantageous as mixing of the reference electrolyte solution and the bulk solution is prevented while there is ion-conductivity between the reference electrolyte solution and the bulk solution when the ion sensor is immersed in the bulk solution.

In an ion sensor according to embodiments of the present disclosure, the reference electrolyte solution may be enclosed by a barrier layer, the barrier layer being ion conductive and being adapted for preventing mixing of the reference electrolyte solution and the bulk solution when the sensor is immersed in the bulk solution. When using a barrier layer, the concentration of the reference ion in the reference electrolyte solution remains stable over a longer time than without the barrier layer.

In embodiments of the present disclosure, the reference electrode and the second electrode may comprise silver chloride. It is an advantage of embodiments of the present disclosure that a silver chloride reference electrode, although continuously immersed in an electrolyte solution, is corrosion resistant. Furthermore, it is easy and inexpensive to manufacture.

In embodiments of the present disclosure, the controller may be adapted for subtracting the second potential difference between the second electrode and the reference electrode from the first potential difference between the first electrode and reference electrode. It is hence possible to eliminate the drift of the voltage of the reference electrode by simple calculations, in particular subtractions.

The controller may comprise a filter for performing a filter operation, in particular for filtering out changes in the second potential difference which have a different behavior than changes caused by the drift of the reference electrode. The drift of the reference electrode is caused by diffusion of the reference ions out of the electrolyte solution. This drift can be modeled. It is an advantage of embodiments of the present disclosure that changes in the second potential difference which are not caused by this drift can be filtered out based on characteristics of the modeled drift. It is an advantage of embodiments of the present disclosure that the output of the filter is representative of the drift of the reference electrode.

The filter may filter out changes in the second potential difference which are faster than the maximum drift speed of the reference electrode. This way, fast concentration changes in the bulk solution which are not representative of the drift of the reference electrode, but which are due to actual concentration changes of the bulk solution, may be filtered out.

In a second aspect, the present disclosure provides the use of an ion sensor according to embodiments of the first aspect of the present disclosure. Features of such ion sensor are set out above. The use may comprise immersing the ion sensor in a bulk solution of which an ion concentration is to be determined, measuring a first potential difference between the first electrode and the reference electrode and a second potential difference between the second electrode and the reference electrode, and compensating for drift of the reference electrode by correcting the first potential difference with the second potential difference.

It is an advantage of embodiments of the present disclosure that it is possible to compensate for the drift of the reference electrode. It is an advantage of embodiments of the present disclosure that the reference electrode can be calibrated to a desired concentration of reference ions in the reference electrolyte solution. In embodiments of the present disclosure the desired concentration of reference ions is reached when, after immersing the ion sensor in the conditioning solution, the potential difference between the second sensor and the reference sensor is zero.

The use according to embodiments of the present disclosure may further comprise, before immersing the ion sensor in a bulk solution of which an ion concentration is to be determined, immersing the ion sensor in a conditioning solution having a pre-determined concentration of reference ions until the concentration of reference ions in the reference electrolyte solution is equal to the predetermined concentration.

In a third aspect, the present disclosure provides a method for compensating for drift in an ion sensor comprising a reference electrode embedded in a reference electrolyte solution comprising reference ions, a first electrode which is ion-selective to the ion to be measured, and a second electrode which is ion-selective to the reference ions or to an ion different from the ion to be measured. The method may comprise measuring a first potential difference between the first electrode and the reference electrode, measuring a second potential difference between the second electrode and the reference electrode, and compensating for drift of the reference electrode by correcting the first potential difference with the second potential difference.

In embodiments of the present disclosure, correcting the first potential difference with the second potential difference may include excluding rapid changes in second potential difference from the compensating step.

Particular and preferred aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

DETAILED DESCRIPTION

Figure 1:
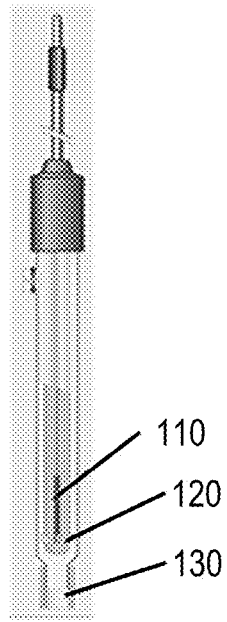
FIG. 1 shows a prior art reference electrode.
Figure 2:
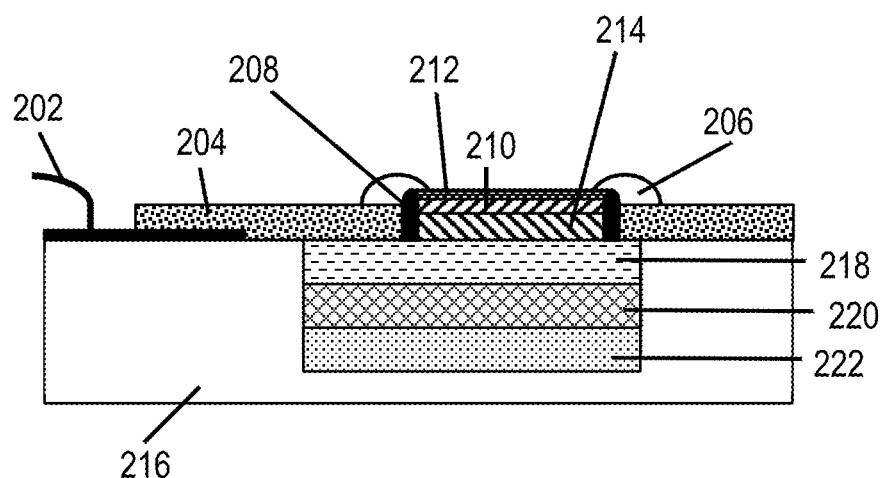
FIG. 2 shows a miniaturized prior art reference electrode.

The present disclosure will be described with respect to particular embodiments and with reference to certain drawings but the disclosure is not limited thereto but only by the claims. The drawings described are only illustrative and are non-limiting. In the drawings, the size of some of the elements may be exaggerated and not drawn to scale for illustrative purposes. The dimensions and the relative dimensions do not correspond to actual reductions to practice of the disclosure.

The terms first, second, and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, bottom, over, under, and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising," used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps, components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

Similarly, it should be appreciated that in the description of example embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is to be understood that embodiments of the disclosure may be practiced without these specific details. In other instances, well-known methods, structures, and techniques have not been shown in detail in order to not obscure an understanding of this description.

In embodiments of the present disclosure where reference is made to the voltage of an electrode, reference is made to the voltage of that electrode with respect to a drift-less large reference electrode.

In embodiments of the present disclosure where reference is made to "a bare electrode," reference is made to an electrode that is in direct contact with the bulk solution when it is immersed in the bulk solution.

Figure 3:
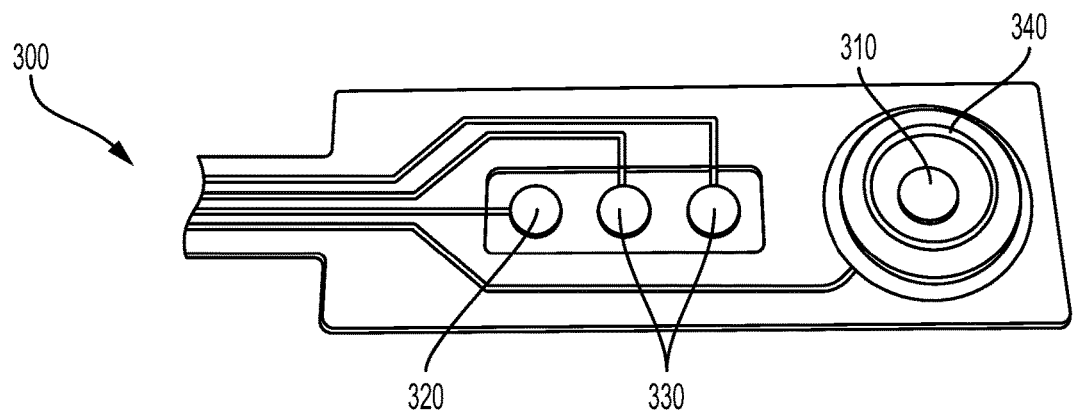
FIG. 3 shows a miniaturized reference electrode and second electrode in accordance with an embodiment of the present disclosure.
Figure 5:
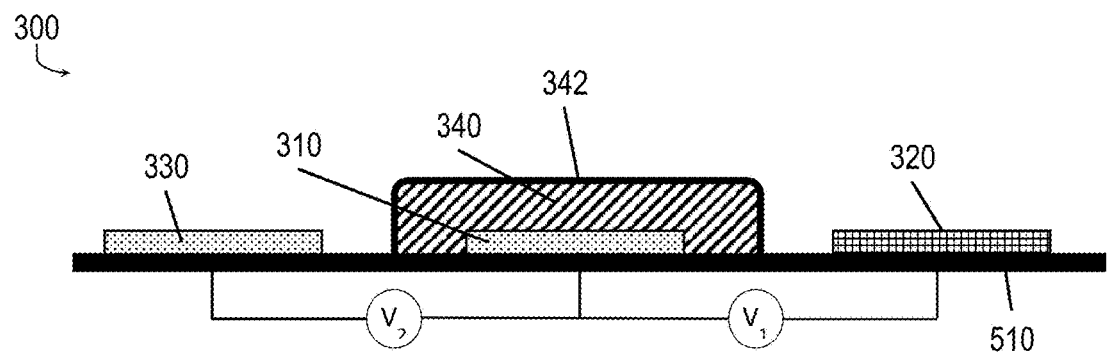
FIG. 5 illustrates a miniaturized ion sensor in accordance with an embodiment of the present disclosure.

In a first aspect, the present disclosure relates to an ion sensor 300, such as a miniaturized ion sensor, for sensing an ion concentration in a bulk solution. An example embodiment of an ion sensor 300 according to embodiments of the present disclosure is illustrated in FIG. 3, and an illustrative cross-sectional view is shown in FIG. 5. The ion sensor 300 as illustrated in FIG. 5 is shown to be integrated on a substrate 510.

In operation, such an ion sensor 300 is immersed in the bulk solution for obtaining the ion concentration of the ion it is sensitive for. In embodiments of the present disclosure, an ion sensor 300 includes at least one reference electrode 310, at least one first electrode 320 which is ion-selective for the ion to be measured, and at least one second electrode 330 which is ion-selective for ions which may leach out of a reference solution surrounding the reference electrode 310, added for performing drift compensation of the first electrode. In the present disclosure, the at least one first electrode 320 and the at least one second electrode 330 share the same at least one reference electrode 310. In the example embodiment illustrated in FIG. 3, the ion sensor 300 includes a single reference electrode 310, a single first electrode 320 and two second electrodes 330.

The reference electrode 310 is embedded in a reference electrolyte solution 340. The material of the reference electrode and the reference electrolyte solution are chosen such that a voltage is induced on the reference electrode 310. This voltage is dependent on the concentration of a reference ion in the reference electrolyte solution. The reference electrode 310 might be any suitable reference electrode, for example, it may be made of Ag/AgCl. The reference electrolyte solution might be any suitable electrolyte solution, such as a KCl solution comprising Cl ions. The present disclosure, however, is not limited to the cited materials. The reference electrode 310 might also be made of copper covered by a reference electrolyte with a fixed concentration of copper ions. Another example is an IrOx electrode covered by a hydrogel containing a buffer. A buffer is a solution with a constant pH that is insensitive to small additions of acid or base.

The volume of the reference electrolyte solution in a miniaturized sensor implementation may typically be a few microliters. The concentration of the chloride ion in the reference KCl solution will determine the reference potential of the reference electrode 310. In embodiments of the present disclosure, the reference electrolyte solution 340 may comprise a hydrogel, such as agarose (agar) or polyhydroxymethylmethacrylate (pHEMA). In embodiments of the present disclosure, the reference electrolyte solution 340 may be a fluid enclosed by a barrier layer 342. The barrier layer 342 may, for instance, be a PVC layer. Presence of a barrier layer 342 is only required if the reference electrolyte solution 340 cannot keep its shape and/or position without being supported. However, even if the reference electrolyte solution is sufficiently stable by itself, a barrier layer 342 may still be provided.

The first electrode 320 is an ion-selective electrode that is selective for the ion to be measured. The ion-selective electrode might, for example, be an ISFET (Ion Sensitive Field Effect Transistor). The ion-selective electrode might, for example, be made of iridium oxide (IrOx) which can be used for pH measurements. The ion-selective electrode 320 can also be an AgCl electrode covered by an ion-selective membrane or self-assembled monolayer. The ion-selective electrode 320 can be an AgCl electrode in contact with an electrolyte reservoir and separated by the sample solution by a glass membrane (thereby forming a pH sensor). The ion-selective electrode 320 can be an AgCl electrode in contact with an electrolyte reservoir and separated by the sample solution by a (solid-state) ion-selective membrane.

When the ion sensor 300 is immersed in the bulk solution, an ion conductive path is present between the reference electrolyte solution 340 and the bulk solution. This is due to used materials, and in particular inexpensive and easy to manufacture materials, always showing some mobility of the ions.

If the ion sensor 300 is placed in a bulk solution with an ion concentration, such as a chloride concentration, that is different from the ion concentration in the reference electrolyte solution 340, ions diffuse into or out of the reference electrolyte solution 340. The diffusion of ions alters the ion concentration in the reference electrolyte solution 340 and leads to drift of the voltage of the reference electrode 310. In a miniaturized ion sensor, the volume of the reference electrolyte solution 340 is much smaller (e.g., three orders of magnitude smaller) than the volume of a reservoir of a reference electrode as represented in FIG. 1 (e.g., microliter versus milliliter volumes). Therefore, the concentration change rate of ions, e.g., chloride ions, in the reference electrolyte solution is higher for miniaturized reference electrodes than for non-miniaturized ones. Also, the voltage change rate of the reference electrode 310 is higher for miniaturized reference electrodes, and the problem of electrode drift is higher for miniaturized ion sensors.

The barrier layer 342, which may optionally be present around the reference electrolyte solution 340, may minimize concentration changes in the reference electrolyte solution 340 by minimizing the transport of ions through the barrier layer 342. Prior art solutions have tried to find barrier layers 342 which are less prone to ion leakage, but this resulted in exotic and expensive materials, which are often difficult to introduce into an existing process flow.

When the ion sensor 300 is immersed in a bulk solution, a first potential difference between the reference electrode 310 and the first electrode 320 is a measure of the ion concentration in the bulk solution. Changes in the concentration of the reference ion in the reference electrolyte solution 340, however, as explained above, change the voltage of the reference electrode 310 and thus the first potential difference between the first electrode 320 and the reference electrode 310.

Figure 4:
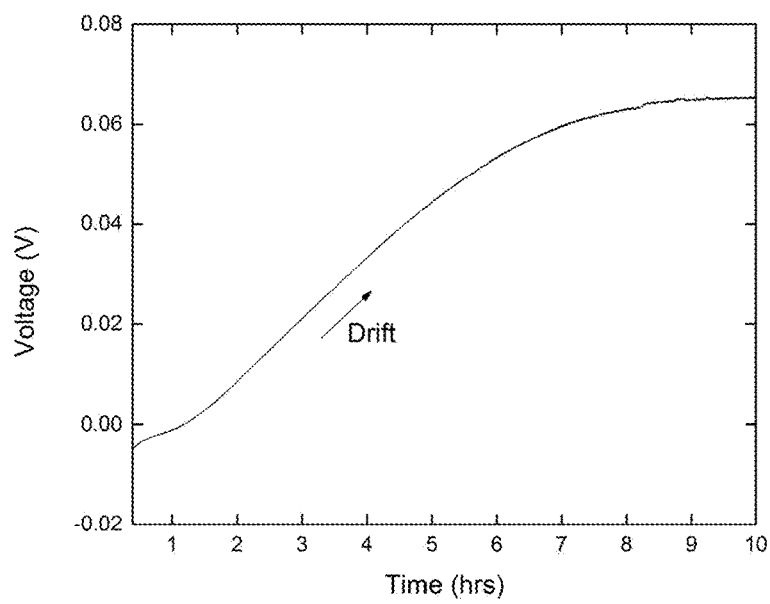
FIG. 4 shows the drift of a reference electrode when immersed in a solution with a different chloride concentration than the chloride concentration in the reference electrolyte solution.

The drift of a miniaturized reference electrode 310 as a function of time is illustrated in FIG. 4. The vertical axis represents the voltage of the reference electrode in volts. The horizontal axis represents the time the reference electrode 310 is submerged in a bulk solution. In this example, the ion concentration, a chloride concentration, in the bulk solution is different from the ion concentration in the reference electrolyte solution. This concentration difference causes the chloride ions to diffuse between the reference electrolyte solution 340 and the bulk solution and therefore causes a drift of the voltage of the reference electrode 310. In FIG. 4, the voltage starts to change almost immediately and increases after about 1 hour for a sufficiently large time (about 8 to 9 hours) until the ion concentrations in the reference solution 340 and in the bulk solution are substantially equal, and the voltage on the reference electrode 310 stabilizes.

To compensate for these voltage changes on the reference electrode causing a faulty determination of the ion concentration in the bulk solution, the ion sensor 300, according to embodiments of the present disclosure, may include a second electrode 330. The second electrode 330 is in direct contact with the bulk solution, as is the first electrode 320, when the ion sensor 300 is immersed in the bulk solution. Therefore, the second electrode is also referred to as a bare electrode. The ion sensor 300, according to embodiments of the present disclosure, may include one or more second electrodes 330, one or more reference electrodes 310, and/or one or more first electrodes 320, including at least one of each.

The second electrode 330 is an ion-selective electrode that is sensitive for the reference ions (e.g., the type of ions leaching out of the reference electrode and causing drift). The second electrode may, for instance, be a bare Ag/AgCl electrode. This second electrode 330 may be less sensitive than the first electrode 320. In one example, the second electrode 330 is not sensitive to the concentration of the ion under study (the ion for which the first electrode 320 is sensitive). In embodiments of the present disclosure, the second potential difference between the second electrode 330 and the reference electrode 310 changes linearly with the logarithm of the concentration of the reference ion in the reference electrolyte solution 340.

Changes in the concentration of the reference ion in the reference electrolyte solution 340 will cause a change in a second potential difference between the second electrode 330 and the reference electrode 310. This change in second potential difference can be used to measure the concentration change of the reference ion in the reference electrolyte solution 340. In embodiments of the present disclosure, this second potential difference is used to compensate for the drift of the reference sensor 310. The second potential difference between the second electrode 330 and the reference electrode 310 is used to correct the determined ion concentration of the bulk solution, which is determined based on the first potential difference between the first electrode 320 and the reference electrode 310. This mitigates the need for a large volume of the reference electrolyte solution 340 or even permits reducing the volume of the reference electrolyte solution, thus reducing the size of the reference electrode 310. An ion sensor 300 according to embodiments of the present disclosure may include a controller for determining a first potential difference between the first electrode 320 and the reference electrode 310 to measure the ion concentration in the bulk solution. Moreover, the controller may be adapted to correct this first potential difference between the first electrode 320 and the reference electrode 310 with a second potential difference between the second electrode 330 and the reference electrode 310, in order to compensate for the drift of the reference electrode 310.

In a second aspect, the present disclosure relates to a method for obtaining an ion concentration in a bulk solution using an ion sensor in accordance with embodiments of the present disclosure.

The method may include an initial, optional, conditioning step where the ion sensor 300 is immersed in a conditioning solution. This conditioning solution may have a reference ion concentration which is the desired reference ion concentration of the reference electrolyte solution 340. During this step, the reference electrode is immersed in the conditioning solution for a time sufficiently long (e.g., until the desired concentration of the reference ion in the reference electrolyte solution is reached). This step is not required if the reference ion concentration was already at the desired level. After this conditioning step, which may be carried out as part of a manufacturing step, or which may be carried out by the user to recalibrate the device, the reference solution 340 has a known ion concentration.

In actual use, the ion sensor 300, according to embodiments of the present disclosure, having a reference electrode 310 immersed or embedded in a reference solution with a known ion concentration, is immersed in the bulk solution. This means that the covered reference electrode 310, the first electrode 320, and the second electrode 330 are all immersed in the bulk solution.

In embodiments of the present disclosure, two potential differences are measured: a first potential difference $V_1$ between the first electrode 320 and the reference electrode 310 (indicative of the ion concentration which needs to be determined) and a second potential difference $V_2$ between the second electrode 330 and the reference electrode 310

(proportional with the ion concentration difference between the reference solution 340 and the bulk solution, and a measure of the drift of the reference electrode 310). When the second potential difference $V_2$ is measured over time it gives an indication of the drift of the reference sensor. The drift of the reference electrode 310 may be compensated for by correcting the first potential difference $V_1$ between the first electrode 320 and the reference electrode 310 with the second potential difference $V_2$ between the second electrode 330 and the reference electrode 310.

In embodiments of the present disclosure, the drift compensation is performed over time by simple calculations, such as by subtracting the measured second potential difference from the first potential difference. More complex solutions which take into account the expected drift behavior are also possible, though. The drift may, for example, be expected to occur at a slow rate. Fast changes of the first and/or second potential differences between the second electrode and the reference electrode may therefore be neglected when compensating for the slow drift. They can, for example, be caused by changing the bulk solution with another bulk solution which has a different reference ion concentration.

Figure 6:
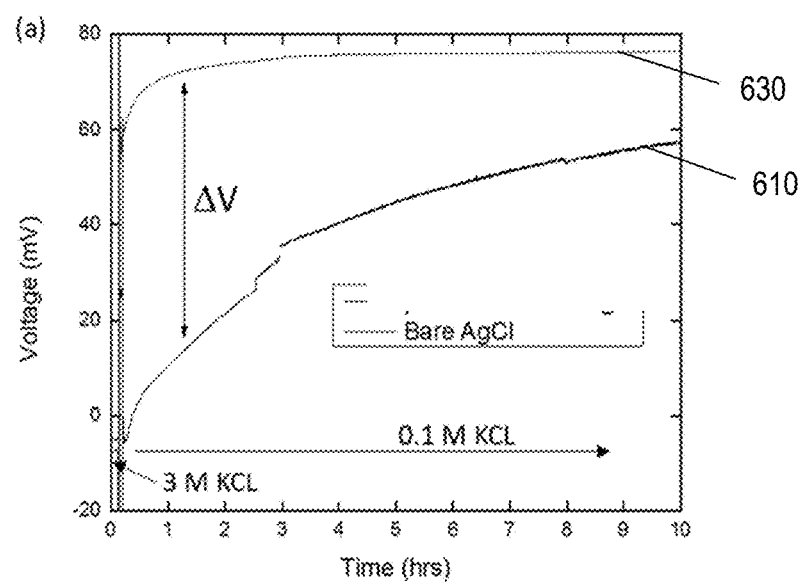
FIG. 6 shows the voltage of a second electrode and the voltage of a reference electrode with respect to a drift-less large reference electrode as functions of time in 3 Molar KCl and in 0.1 Molar KCl, where the second electrode and the reference electrode are configured in accordance with an embodiment of the present disclosure.

FIG. 6 shows in a first trend line 610 the voltage of a bare AgCl electrode 330 (the second electrode) and in a second trend line 630 the voltage a pHEMA covered AgCl electrode 310 (the reference electrode) over time. In a first conditioning step, the second electrode and the reference electrode may be immersed and conditioned in 3M KCl. The reference electrode and the second electrode are immersed in 3M KCl until the chloride concentration in the pHEMA is equal to 3M KCl. Next, the reference electrode and the second electrode may be immersed in 0.1M KCl. In 3M KCl, the voltages are close to 0 mV, as expected, because there is no difference in chloride concentration between both solutions. When immersed in 0.1M KCl, the bare AgCl electrode (the second electrode 330) rapidly changes potential to about 70 mV, while the pHEMA covered AgCl electrode (the reference electrode 310) slowly approaches the same potential as chloride ions diffuse out of the reservoir (the reference electrolyte solution 340).

Figure 7:
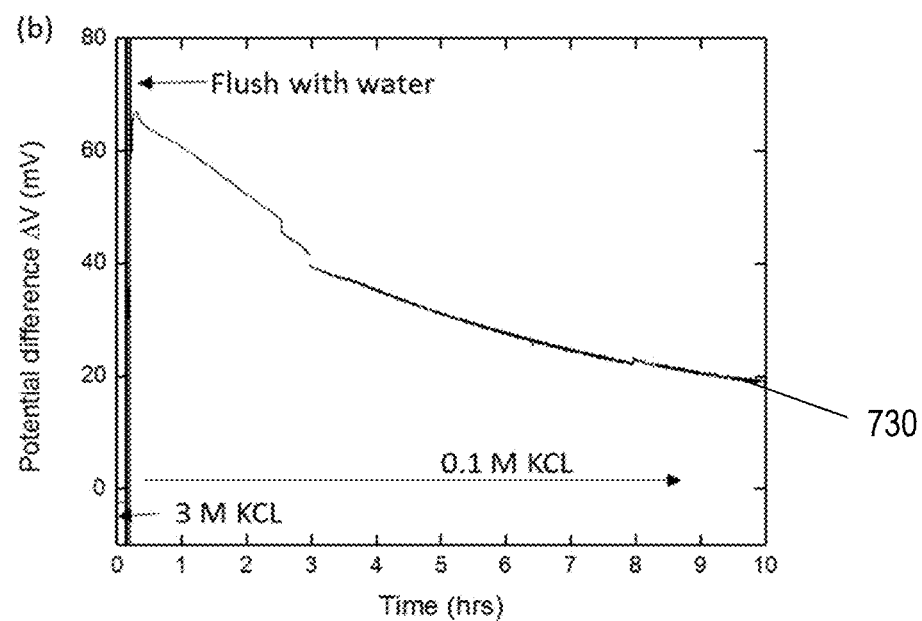
FIG. 7 shows the potential difference between the two traces of FIG. 6.

In FIG. 7, a trend line 730 is plotted indicating the difference between the first trend line 610 and second trend line 630 in FIG. 6, which is indicative of $V_2$ in FIG. 4, for the system of FIG. 6 with the reference electrode 310 and the second electrode 330. The potential difference is ~0 mV in 3M KCL, increases rapidly when immersed in 0.1 M KCl and slowly returns toward 0 mV as the pHEMA reservoir (the reference electrolyte solution) equilibrates with the bulk solution. This signal can be used to compensate for the drift of the reference electrode 310.

Figure 8:
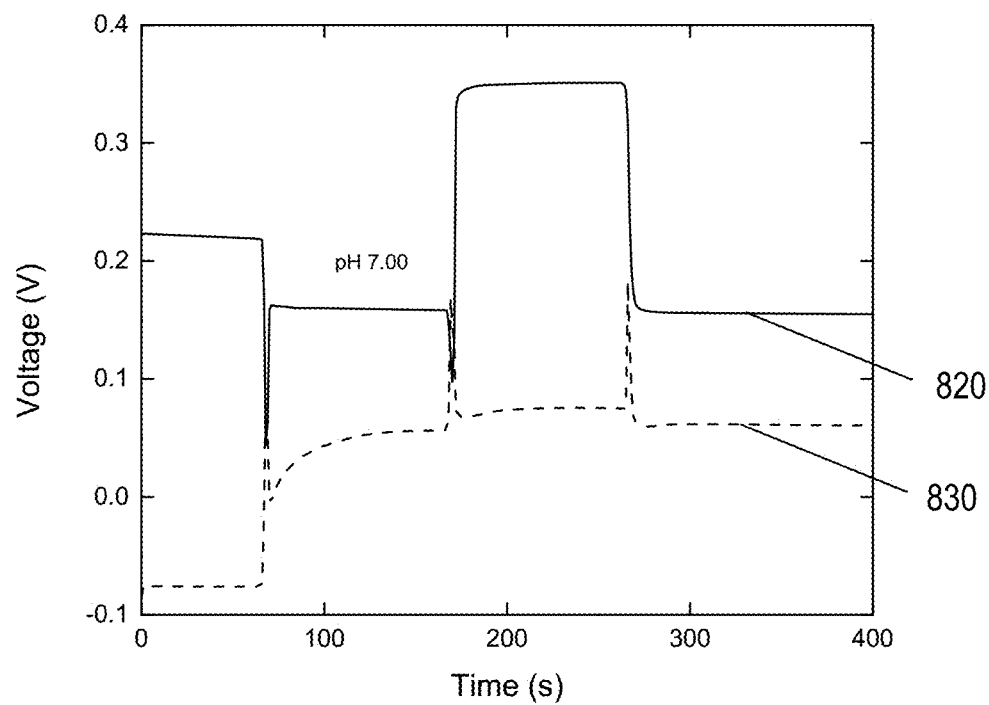
FIG. 8 shows the potential difference between an IrOx electrode and a reference electrode after compensation for the drift of the reference electrode and the potential difference between a bare AgCl electrode and the reference electrode as functions of time measured with an ion sensor in accordance with embodiments of the present disclosure.

Curve 820 in FIG. 8 shows the potential difference $V_1$ between a first electrode 320 and a reference electrode 310 as a function of time. The first electrode 320 is, in this case, an IrOx electrode. The high level voltage in curve 820 corresponds with a bulk solution having a pH of 4.00. The low level voltages in curve 820 correspond with a bulk solution having a pH of 7.00.

Curve 830 in FIG. 8 corresponds with the potential difference $V_2$ between the second electrode 330 and the reference electrode 310. In this case, the reference electrode 310 is an AgCl electrode. The second electrode 330 is less sensitive to the pH of the bulk solution than the first electrode 320 (6 mV/pH compared with 64 mV/pH) and can therefore be used to compensate for the drift of the reference electrode 310. The first electrode has a much higher pH sensitivity of 64 mV/pH.

In a first conditioning step, the ion sensor 300 may be immersed in a 3M KCl bulk solution. This can be seen in the first 70 seconds in the curves of FIG. 8. Next the ion sensor may be calibrated by alternatingly immersing it in a pH 7.00 buffer and a pH 4.00 buffer, both containing 0.1M KCl. The potential difference of curve 830 is increasing because the chloride concentration in the reference electrolyte solution 340 and the sample solution is different (3M in the reference electrolyte and 0.1M in the sample).

Figure 9:
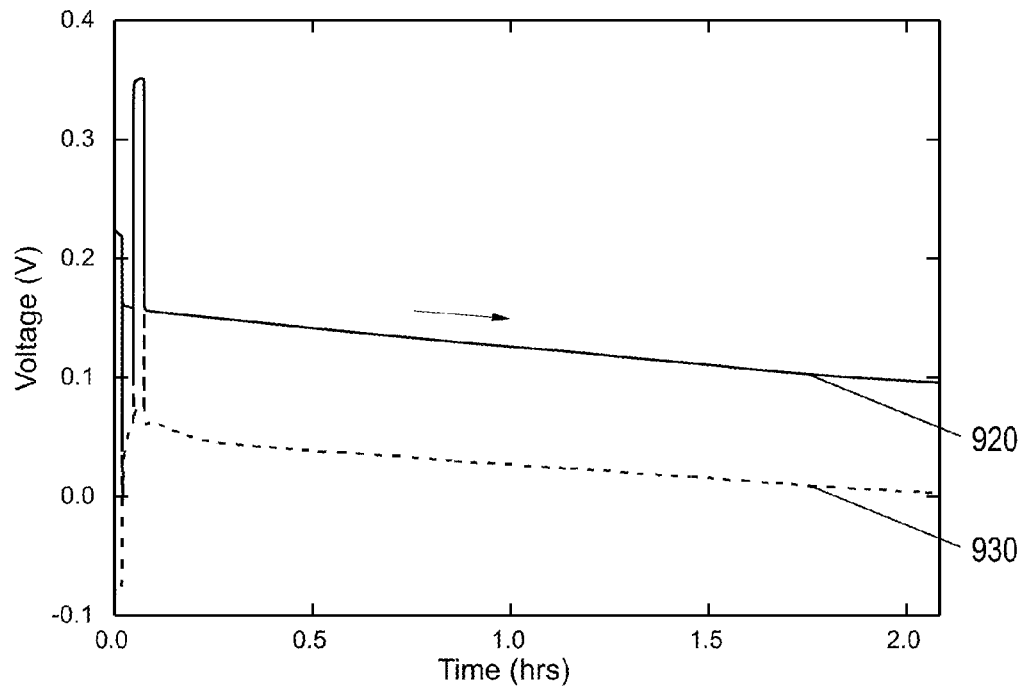
FIG. 9 shows the potential difference between an IrOx electrode and a reference electrode and the potential difference between a bare AgCl electrode and the reference electrode as functions of time measured with an ion sensor in accordance with embodiments of the present disclosure.

FIG. 9 shows two curves. A first curve 920 illustrates the potential difference $V_1$ between the first electrode 320 and the reference electrode 310. The second curve 930 shows the potential difference $V_2$ between the second electrode 330 and the reference electrode 310. The peaks in the first curve 920 and the second curve 930 are caused by the calibration of the miniaturized ion sensor 300. The first curve and the second curve show approximately the same drift over time. This drift is caused by a drift of the reference electrode 310. In the example of FIG. 9, the miniaturized ion sensor is immersed in a bulk solution with pH 7.00 and with 0.1M KCl. The reference electrolyte solution 340 was conditioned in 3M KCl. Therefore, the chloride ions leach out of the reference electrolyte solution 340 (pHEMA reservoir in this example embodiment of the present disclosure) when the miniaturized ion sensor 300 is immersed in the bulk solution. This causes a drift of the reference electrode 310, which is visible in curve 920 and curve 930. In the example of FIG. 9, this drift can be compensated for by subtracting the drift of the second curve 930 from the first curve 920.

Figure 10:
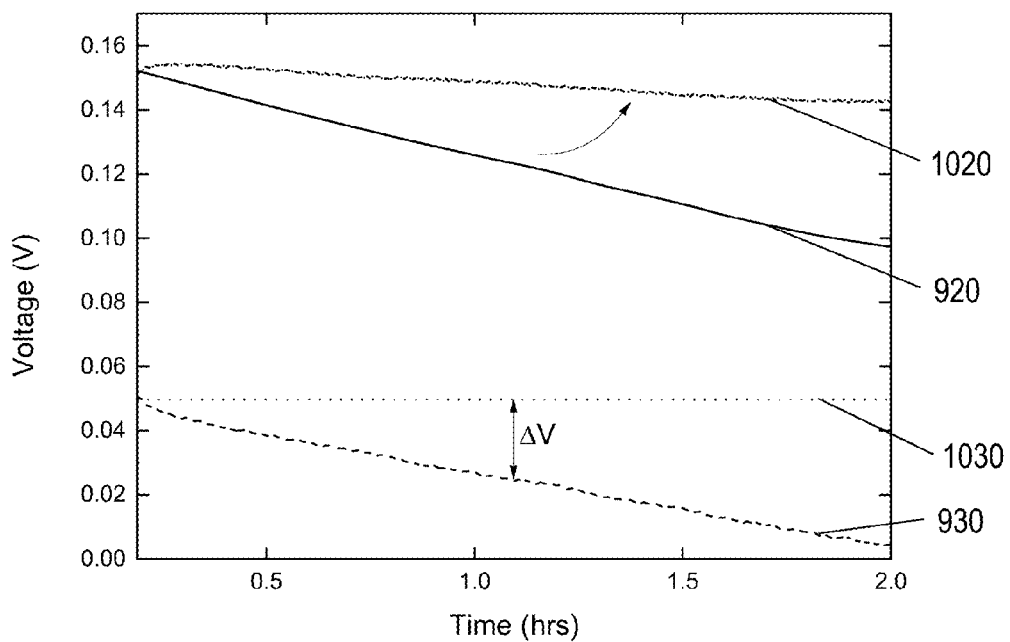
FIG. 10 shows how to compensate for drift of the reference electrode in accordance with embodiments of the present disclosure.

This is illustrated in FIG. 10 which shows the first curve 920, which is the potential difference $V_1$ between the first electrode 320 and the reference electrode 310 as a function of time. FIG. 10 also shows the second curve 930 which is the potential difference $V_2$ between the second electrode 330 and the reference electrode 310. Both curves have a negative slope caused by the leaching out of reference ions out of the reference electrolyte solution 340. This slope can be removed from the measurement curve 920 by adding the drift voltage to the first curve 920, resulting in curve 1020. The drift voltage at a certain moment in time is the potential difference between the curve 1030 and the second curve 930, whereby the curve 1030 has a constant voltage, which is the voltage of the second curve 1030 at the beginning of the measurement. It can be seen that the slope of curve 1020 is significantly decreased compared to the slope of curve 920. It is thus an advantage of embodiments of the present disclosure that the drift of the reference electrode 310 caused by leaching out of reference ions can be compensated for at least partially by measuring and taking into account the potential difference $V_2$ between a second electrode 330 and the reference electrode 310 whereby the second electrode 330 is ion-selective for the reference ion present in the reference electrolyte surrounding the reference electrode 310, and whereby the second electrode 330 is in direct contact with the bulk solution.

Figure 11:
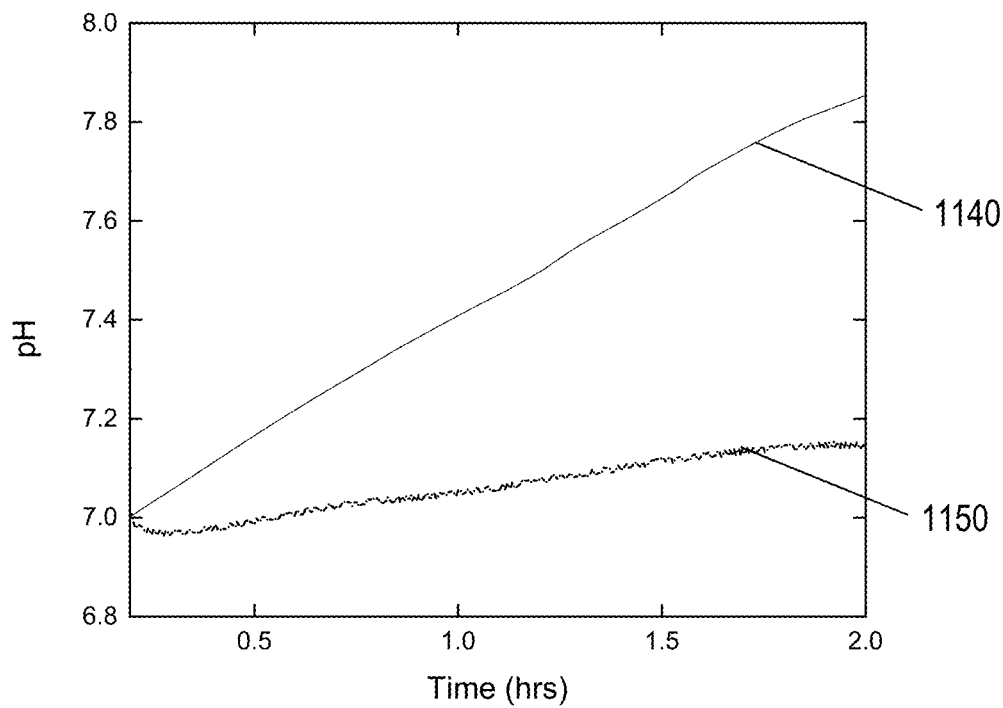
FIG. 11 shows the measured pH before and after compensating for drift in accordance with embodiments of the present disclosure.

FIG. 11 shows the pH value which is derived from the measured potential difference between the first electrode 320 and the reference electrode 310 (curve 920 in FIG. 10). This derivation can be done by calibrating the ion sensor 300 in one or more bulk solutions with known pH value. The resulting pH value curve is curve 1140. After compensating for drift of the reference electrode 310, curve 1150 is obtained. Without compensation, a 0.85 pH point offset is reached after two hours, whereas only a 0.15 pH point offset is reached with compensation.

FIG. 12, FIG. 13, FIG. 14 and FIG. 15 illustrate measurements taken with a different (compared to the ion sensor used in the experiments illustrated in FIGS. 8-11) ion sensor in accordance with an embodiment of the present disclosure.

Figure 12:
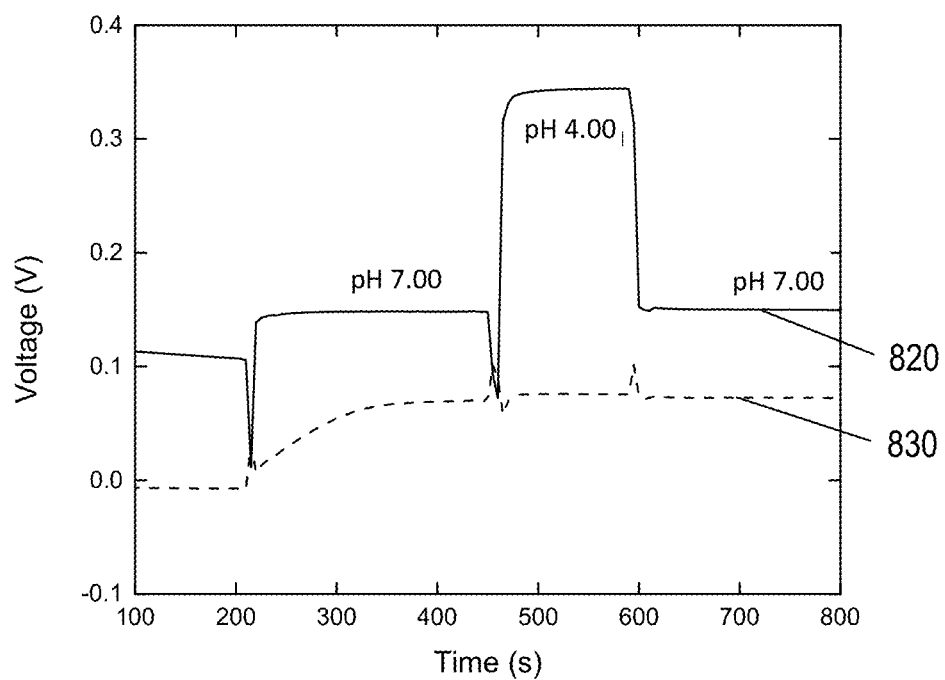
FIG. 12 shows the potential difference between an IrOx electrode and a reference electrode after compensation for the drift of the reference electrode and the potential difference between a bare AgCl electrode and the reference electrode as functions of time measured with an ion sensor in accordance with embodiments of the present disclosure.

Curve 820 in FIG. 12 shows the potential difference of the first electrode 320 and the reference electrode 310. The first electrode 320 is, in this case, an IrOx electrode. The high level voltage in curve 820 corresponds with a bulk solution having a pH of 4.00. The low level voltage in curve 820 corresponds with a bulk solution having a pH of 7.00. Curve 830 corresponds with the potential difference between the second electrode 330 and the reference electrode 310. In this case, the reference electrode 310 is an AgCl electrode. The conditioning of the ion sensor is done in a 3M KCl bulk solution. The calibration is done in a buffer with a pH of 7 and in a buffer with a pH of 4. Both buffers contain 0.1 M KCl. The IrOx electrode has a sensitivity of 65 mV/pH, and the bare AgCl electrode is substantially insensitive for pH changes (only 2 mV/pH).

Figure 13:
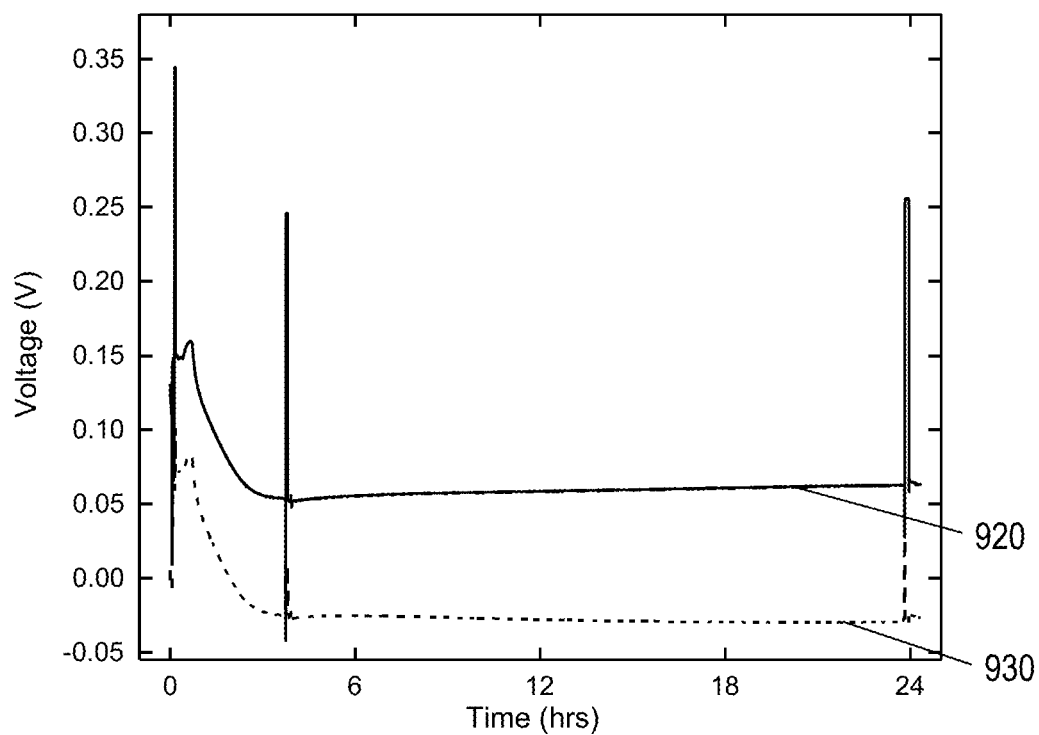
FIG. 13 shows the potential difference between an IrOx electrode and a reference electrode and the potential difference between a bare AgCl electrode and the reference electrode as functions of time measured with an ion sensor in accordance with embodiments of the present disclosure.

FIG. 13 shows a first curve 920, which is the potential difference between the first electrode 320 and the reference electrode 310, and a second curve 930, which is the potential difference between the second electrode 330 and the reference electrode 310. The pHEMA reservoir of the reference electrode 310 was conditioned in a buffer with 3M KCl. The curves in FIG. 13 result from immersing the ion sensor in a sample solution with a pH of 7 and with 0.1M KCl. The concentration difference causes the drift of the reference electrode 310 during the first 4 hours. The peaks in the curves after 4 hours, and after 24 hours are caused by immersing the ion sensor in a buffer with a pH of 4. The pH sensitivity of the first electrode 320 (the IrOx electrode) is: 65 mV/pH at 0 hr, 64 mV/pH at 4 hrs, and 64 mV/pH at 24 hrs. The pH sensitivity of the second electrode 330 (the bare AgCl electrode) is: 2 mV/pH at 0 hr, 1 mV/pH at 4 hrs, and 1 mV/pH at 24 hrs. As can been seen from these measurements, this ion sensor has no sensitivity loss after 24 hrs.

Figure 14:
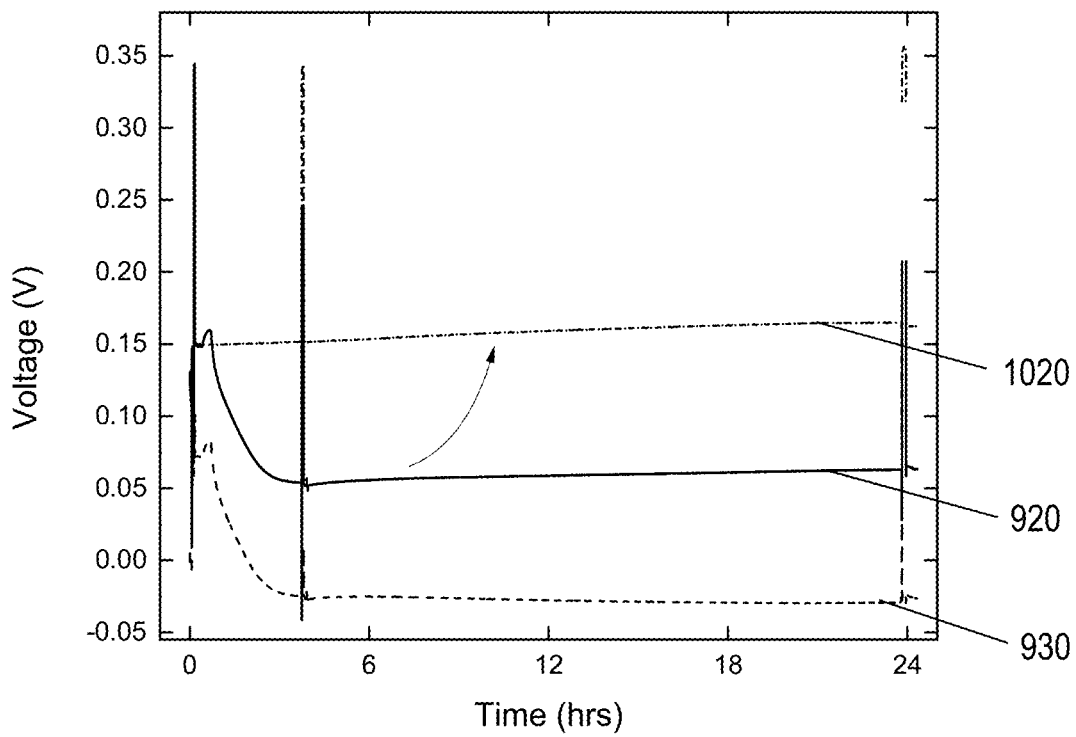
FIG. 14 shows how to compensate for drift of the reference electrode in accordance with embodiments of the present disclosure.

FIG. 14 shows the voltage measured with the IrOx electrode (curve 920), the voltage measured with the bare AgCl electrode (curve 930), and the curve 1020 which is the result of compensating the voltage measured with the IrOx electrode with the voltage with the bare AgCl electrode. The voltages are measured with the reference electrode 310 as reference. The compensation is done to remove the drift of the reference electrode.

Figure 15:
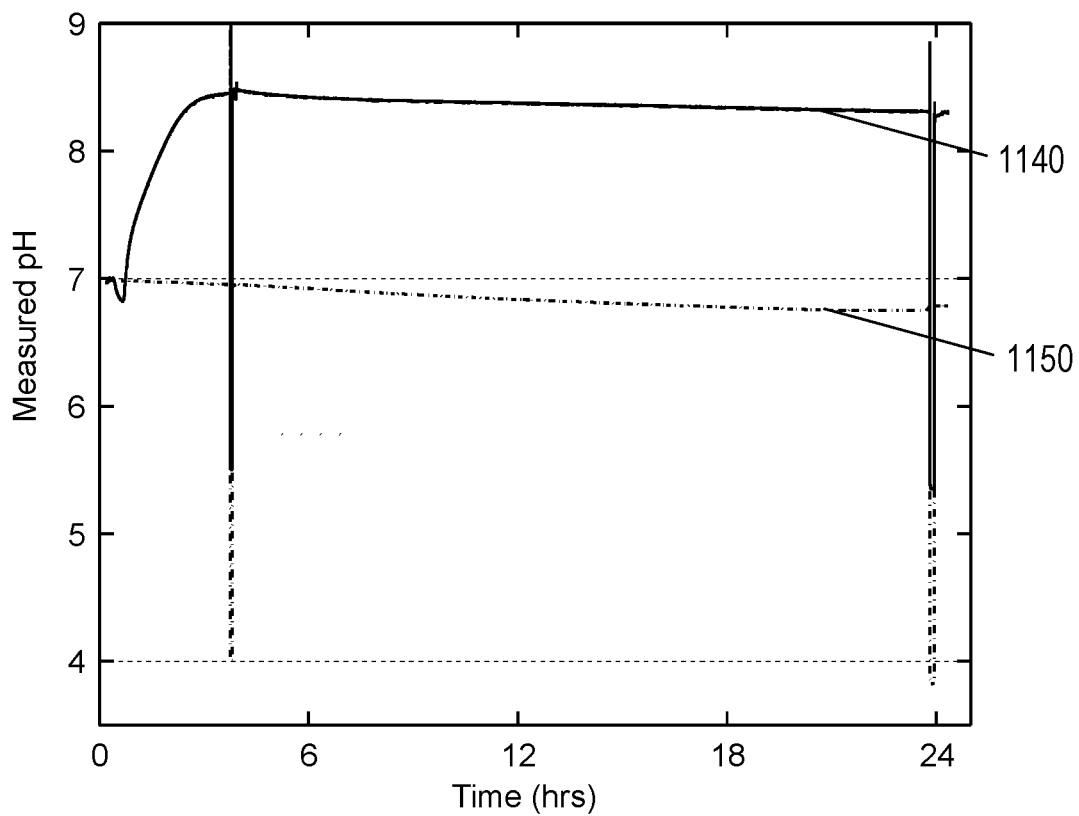
FIG. 15 shows the measured pH before and after compensating for drift in accordance with embodiments of the present disclosure.

FIG. 15 shows the pH value over time, derived from the measured voltages in FIG. 14. The conversion from a voltage to a pH value can be done based on the calibration measurements. Curve 1140 is the measured pH value corresponding with the measured voltage of curve 920. Curve 1150 is the obtained pH value after correcting for the drift of the reference electrode. Without compensation, the measured pH is equal to: 1.5 after 4 hrs and 1.3 after 24 hrs. With compensation, the measured pH is equal to: 0.04 after 4 hrs and 0.2 after 24 hrs. It can be seen from FIG. 15 that the drift of the reference electrode during the first 4 hours, which is visible in curve 1140, can be removed by compensating for it (curve 1150). The drift between hour 4 and hour 24 might be caused by a pH change in the calibration solution (e.g. by evaporation), or by a temperature change.

Figure 16:
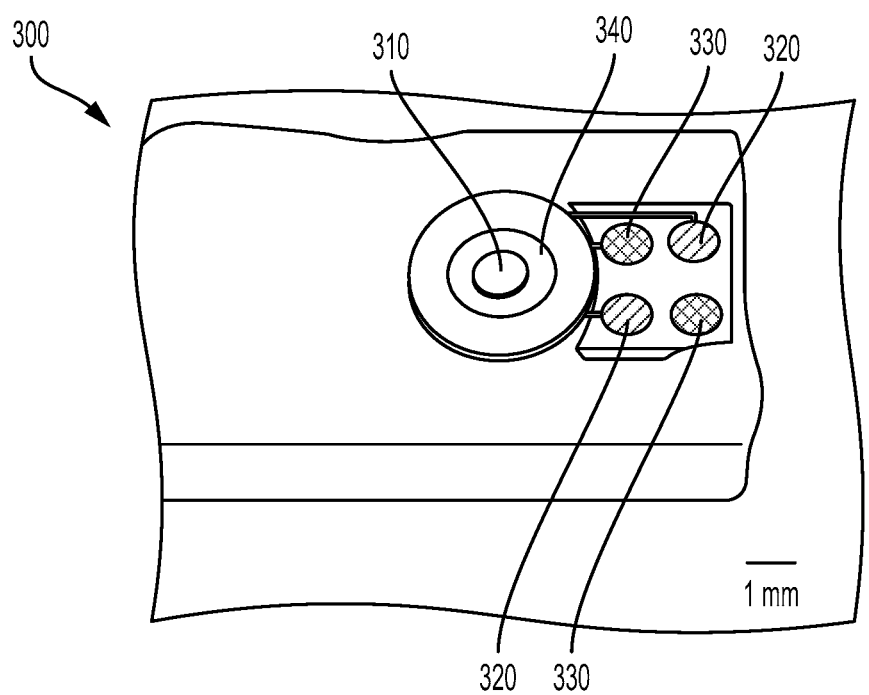
FIG. 16 shows a sensor according to an example embodiment of the present disclosure.

FIG. 16 shows a picture of a miniaturized ion sensor 300 in accordance with an embodiment of the present disclosure. The picture shows a reference electrode 310 embedded in a reference electrolyte solution 340 (KCl in pHEMA reservoir). The reference electrode 310 is an AgCl electrode. FIG. 16 also shows two first electrodes 310 and two second electrodes 320. In this example embodiment of the present disclosure, the first electrodes 310 are IrOx electrodes and the second electrodes are bare AgCl electrodes.

In an example embodiment of the present disclosure, the drift of the reference electrode 310 may be compensated for using the formulas below. In the following formulas, $V_1$ is the voltage difference between the first electrode 320 and the reference electrode 310. $V_2$ is the voltage difference between the second electrode 330 and the same reference electrode 310.

In the examples below, the reference electrode 310 is an AgCl electrode in pHEMA comprising KCl, the first electrode 320 is a pH sensitive (IrOx) electrode, and the second electrode 330 is an AgCl electrode. The methods applied in the example below can, however, also be applied to other ion sensors 300 in accordance with embodiments of the present disclosure.

In the following formulas, time instance zero corresponds with the moment immediately after calibrating the ion sensor 300 in a 3M KCl solution.

After calibration (t=0):

$$V_1(t=0) = V\text{pH} - V\text{pHEMA}(3M)$$

$$V_2(t=0) = V\text{Cl(unknown Cl---)} - V\text{pHEMA}(3M)$$

where 3M is the known concentration in the pHEMA solution.

After leaching out of ions from the electrolyte solution 340 (the pHEMA reservoir), at $t=t_1$:

$$V_1(t=t_1) = V\text{pH} - V\text{pHEMA}(3M-\delta)$$

$$V_2(t=t_1) = V\text{Cl(unknown Cl---)} - V\text{pHEMA}(3M-\delta)$$

without compensation.

In this case, $V_1$ has an unknown offset and is therefore not a correct measure for the pH anymore. However, $V_2$ exhibits a similar offset. It is possible to compensate for the offset with the value of $V_2$ recorded at t=0:

$$V_2(t=0) - V_2(t=t_1) = V\text{Cl(unknown Cl---)} - V\text{pHEMA}(3M) - (V\text{Cl(unknown Cl---)} - V\text{pHEMA}(3M-\delta))$$
$$= V\text{pHEMA}(3M-\delta) - V\text{pHEMA}(3M)$$

Figure 17:
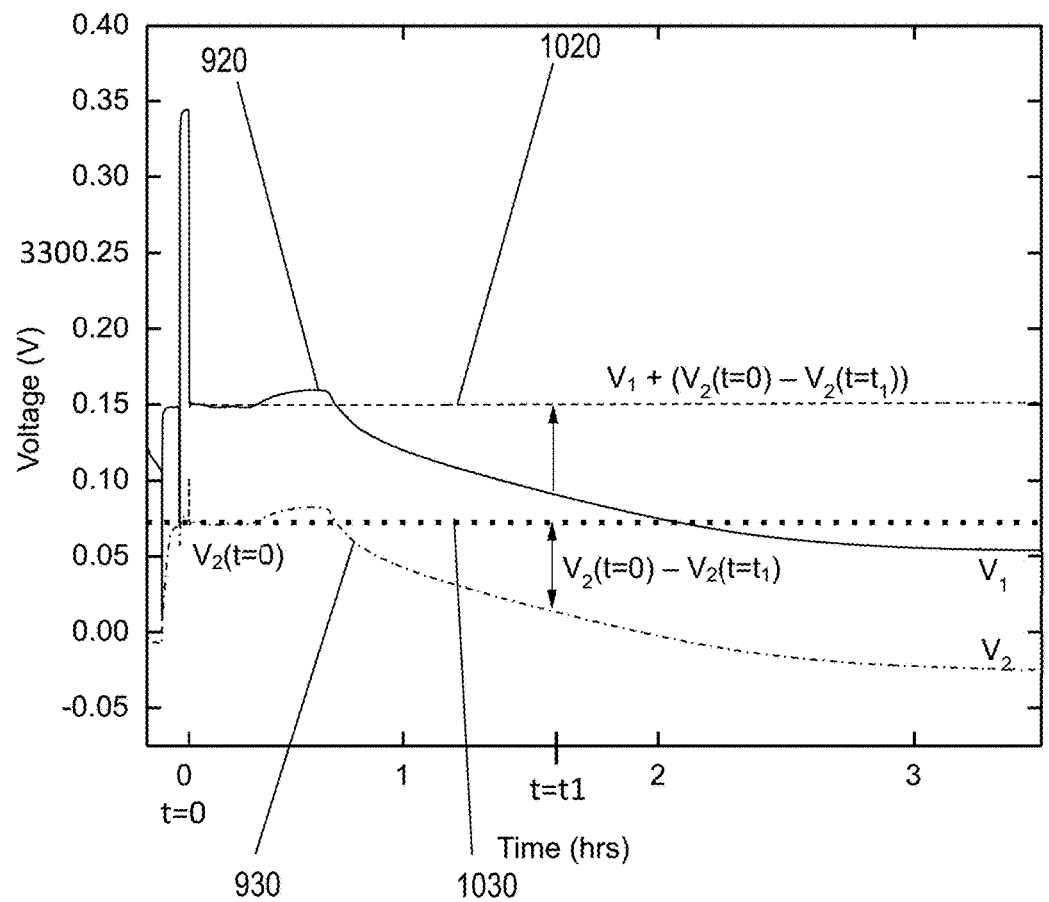
FIG. 17 shows the potential difference between an IrOx electrode and a reference electrode and the potential difference between a bare AgCl electrode and the reference electrode as functions of time, measured with an ion sensor in accordance with embodiments of the present disclosure.

This difference can be used to compensate for the drift of $V_1$ resulting in a compensated $V_1$, which may be used to determine the pH. In this example it is assumed that the Cl— concentration at time t=0 is equal to the Cl— concentration at time $t=t_1$. These formulas are illustrated in the graph of FIG. 17 where $V_1$ and $V_2$ are plotted as functions of time.

In embodiments of the present disclosure, compensation for the drift is done as explained in the following paragraphs. The voltages $V_1$ and $V_2$ depend on the pH and chloride concentration:

$$V_1 = d\text{ pH} - a\text{ pCl(pHEMA)} + C_1$$

$$V_2 = b\text{ pCl(sample)} - a\text{ pCl(pHEMA)} + C_2$$

wherein pCl(pHEMA) is defined as a negative logarithm (−log) of the chloride concentration in the pHEMA, pCl (sample) is a negative logarithm of the chloride concentration in the sample, a, b, and d are the sensitivities towards chloride and pH, respectively, which are close to the Nernstian limit of 59 mV/decade, and $C_1$ and $C_2$ are constants given by the standard potentials of the interface reactions involved.

However, $V_1$ and $V_2$ change over time:

$$\frac{dV_1}{dt} = d\frac{dpH}{dt} - a\frac{dpCl(pHEMA)}{dt}$$

wherein $$a\frac{dpCl(pHEMA)}{dt}$$

is the drift and $$d\frac{dpH}{dt}$$

is the signal.

$$\frac{dV_2}{dt} = b\frac{dpCl(\text{sample})}{dt} - a\frac{dpCl(pHEMA)}{dt}$$

wherein $$a\frac{dpCl(pHEMA)}{dt}$$

is the drift leaching out of chloride of pHEMA gel (slow effect) and wherein $$b\frac{dpCl(\text{sample})}{dt}$$

is the change in the chloride concentration in the bulk solution.

$V_2$ changes over time if the chloride concentration in the sample changes over time, or if ions leach out of the pHEMA reservoir, which is the drift term. $V_1$ changes over time because of pH changes in sample, which is the parameter to be measured, or because of the same drift term.

If the chloride concentration in the sample (pCl(sample)) does not change, $V_2$ can be directly used to compensate $V_1$ as described above.

Figure 18:
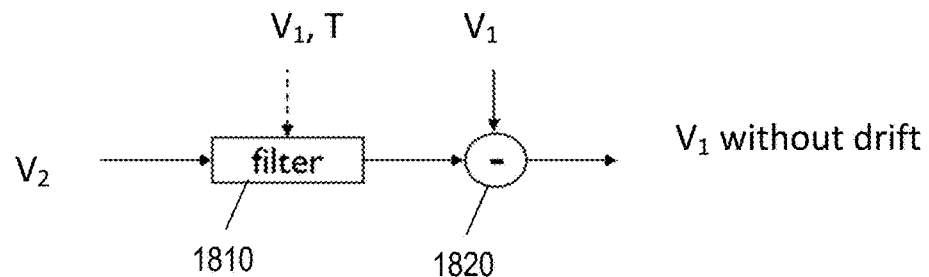
FIG. 18 shows a signal processing flow in accordance with embodiments of the present disclosure.

The pHEMA reservoir is a hydrogel that slows the diffusion of the chloride ions. Therefore, the drift term $$\frac{dpCl(pHema)}{dt}$$

will be small (for instance <10 mV/min or smaller). A rapid change in $V_2$ is therefore most likely to be attributed to changes in the sample chloride concentration. These changes do not need to be compensated for. Therefore, rapid changes can be removed by first applying a filter 1810, as illustrated in FIG. 18, to $V_2$.

The filter 1810 may be implemented as a software filter running on a processor/controller, or it may be implemented as a hardware filter. This filter 1810 can be used to cancel noise caused by measurement electronics and/or changes in the sample chloride concentration. As shown in FIG. 18, this filter is applied to the $V_2$ signal, after which the filtered $V_2$ is used to compensate for the drift of $V_1$ (the minus operator 1820 in FIG. 18). Amongst others, the filter 1810 may be an (extended) Kalman filter, a particle-filter (a filter based on Sequential Monte Carlo methods or density estimation algorithms), a Wiener-filter, or a 'plain' digital filter.

In embodiments of the present disclosure, the filter 1810 may have other input signals such as a temperature input, the signal $V_1$, or signals from other sensors. The filter 1810 might, for example, be a Kalman filter. Based on these inputs, the filter 1810 estimates the most likely drift signal which can afterwards be subtracted from $V_1$. These additional inputs are shown in FIG. 18 with a dashed arrow.

The filter 1810 (e.g., Kalman or particle filter) may estimate the most likely drift of the reference electrode 310 based on a physical model of the drift and may filter out noise caused by the measurement electronics or changes in the chloride concentration in the bulk solution. In embodiments of the present disclosure the filter 1810 or combination of filters 1810 is recursive, meaning that the filter 1810 uses current and past measurements to predict the most likely drift.

Figure 19:
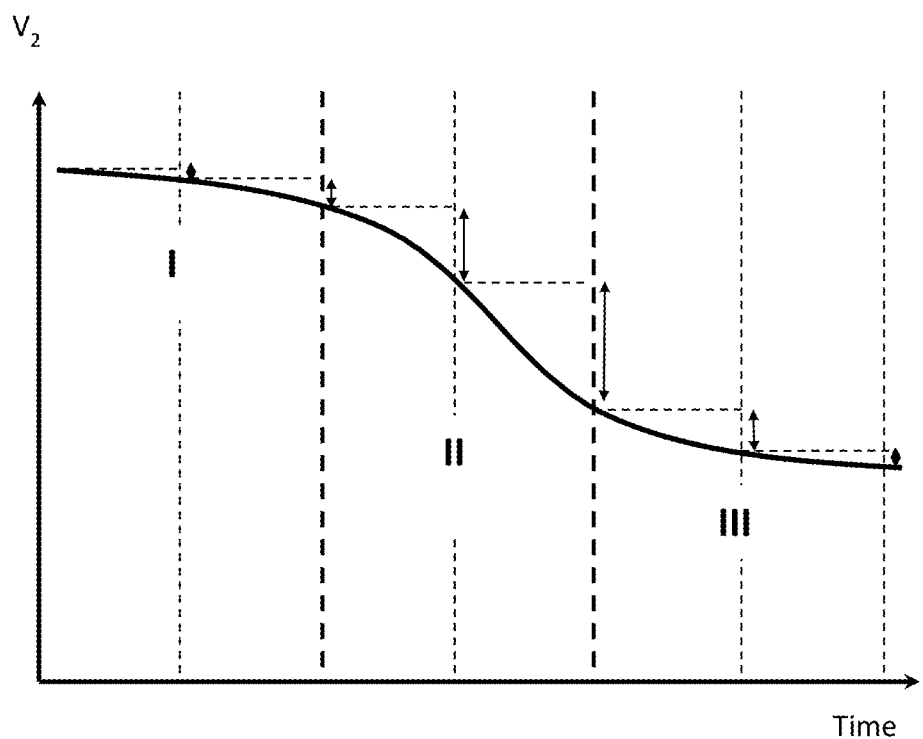
FIG. 19 shows the potential difference between a bare AgCl electrode and the reference electrode as a function of time measured with an ion sensor in accordance with embodiments of the present disclosure.

In embodiments of the present disclosure, the decision to compensate (the subtraction operator 1820 in FIG. 18) the filtered signal can be conditional as well. If $V_2$ or its derivative does not exceed a predetermined threshold, $V_1$ is compensated. This is illustrated in FIG. 19. FIG. 19 shows $V_2$ as a function of time. In regions I and III the slope is below a certain threshold. In these regions, $V_1$ may be compensated with $V_2$. In region II, The slope is above a certain threshold. In this region $V_1$ may not be compensated by $V_2$.

What is claimed is:

1. An ion sensor for sensing ions in a bulk solution, the ion sensor comprising:
   a reference electrode embedded in a reference electrolyte solution comprising reference ions, wherein the reference electrolyte solution induces a voltage on the reference electrode, and wherein the induced voltage is dependent on a concentration of reference ions in the reference electrolyte solution;
   a first electrode which is ion-selective to the ions in the bulk solution;
   a second electrode which is ion-selective to an ion different from the ions in the bulk solution, wherein the first electrode and the second electrode are in direct contact with the bulk solution when the ion sensor is immersed in the bulk solution; and
   a controller configured to carry out operations comprising:
      determining a first potential difference between the first electrode and the reference electrode, wherein the first potential difference is dependent on a concentration of the ions in the bulk solution;
      determining a second potential difference between the second electrode and the reference electrode; and
      correcting the first potential difference between the first electrode and the reference electrode with the second potential difference between the second electrode and the reference electrode to compensate for a drift of the voltage induced on the reference electrode.

2. The ion sensor of claim 1, wherein the reference electrolyte solution comprises a hydrogel.

3. The ion sensor of claim 1, wherein the reference electrolyte solution is enclosed by a barrier layer, the barrier layer being ion conductive and configured to prevent mixing of the reference electrolyte solution and the bulk solution when the ion sensor is immersed in the bulk solution.

4. The ion sensor of claim 1, wherein the reference electrode and the second electrode comprise silver chloride.

5. The ion sensor of claim 1, wherein correcting the first potential difference with the second potential difference comprises subtracting the second potential difference from the first potential difference.

6. The ion sensor of claim 1, wherein the operations further comprise filtering out changes in the second potential difference which are different from changes caused by the drift of the reference electrode.

7. The ion sensor of claim 6, wherein filtering out changes in the second potential difference comprises filtering out changes in the second potential difference which are faster than a maximum drift rate of the reference electrode.

8. A method comprising:
providing an ion sensor comprising:
a reference electrode embedded in a reference electrolyte solution comprising reference ions, the reference electrolyte solution inducing a voltage on the reference electrode, wherein the induced voltage is dependent on a concentration of reference ions in the reference electrolyte solution;
a first electrode which is ion-selective to ions in a bulk solution; and
a second electrode which is ion-selective to an ion different from the ions in the bulk solution;
immersing the ion sensor in the bulk solution, wherein the first electrode and the second electrode are in direct contact with the bulk solution;
measuring a first potential difference between the first electrode and the reference electrode, and a second potential difference between the second electrode and the reference electrode; and
compensating for a drift of the reference electrode by correcting the first potential difference with the second potential difference.

9. The method of claim 8, further comprising, before immersing the ion sensor in the bulk solution, immersing the ion sensor in a conditioning solution having a pre-determined concentration of the reference ions until the concentration of the reference ions in the reference electrolyte solution is equal to the pre-determined concentration.

10. The method of claim 8, wherein the reference electrolyte solution comprises a hydrogel.

11. The method of claim 8, wherein the reference electrolyte solution is enclosed by a barrier layer, the barrier layer being ion conductive and configured to prevent mixing of the reference electrolyte solution and the bulk solution when the ion sensor is immersed in the bulk solution.

12. The method of claim 8, wherein the reference electrode and the second electrode comprise silver chloride.

13. The method of claim 8, wherein correcting the first potential difference with the second potential difference comprises subtracting the second potential difference from the first potential difference.

14. The method of claim 8, wherein correcting the first potential difference with the second potential difference comprises filtering out changes in the second potential difference which are different from changes caused by the drift of the reference electrode.

15. The method of claim 14, wherein correcting the first potential difference with the second potential difference comprises filtering out changes in the second potential difference which are faster than a maximum drift rate of the reference electrode.

* * * * *